(12) United States Patent
Katsevich et al.

(10) Patent No.: US 8,929,637 B1
(45) Date of Patent: Jan. 6, 2015

(54) SYSTEM AND METHOD OF VARIABLE FILTER LENGTH LOCAL TOMOGRAPHY

(71) Applicants: University of Central Florida Research Foundation, Inc., Orlando, FL (US); iTomography Corporation, Barker, TX (US)

(72) Inventors: Alexander Katsevich, Oviedo, FL (US); Michael Frenkel, Barker, TX (US)

(73) Assignees: University of Central Florida Research Foundation, Inc., Orlando, FL (US); iTomography Corporation, Barker, TX (US)

( * ) Notice: Subject to any disclaimer, the term of this patent is extended or adjusted under 35 U.S.C. 154(b) by 0 days.

(21) Appl. No.: 14/080,099

(22) Filed: Nov. 14, 2013

Related U.S. Application Data

(63) Continuation-in-part of application No. 13/722,383, filed on Dec. 20, 2012, now Pat. No. 8,611,631.

(51) Int. Cl.
G06K 9/00 (2006.01)
G06T 11/00 (2006.01)
A61B 6/10 (2006.01)

(52) U.S. Cl.
CPC .............. *G06T 11/003* (2013.01); *A61B 6/10* (2013.01)
USPC ........................................................ 382/131

(58) Field of Classification Search
None
See application file for complete search history.

(56) References Cited

U.S. PATENT DOCUMENTS

| | | | |
|---|---|---|---|
| 5,539,800 A | 7/1996 | Katsevich et al. |
| 5,550,892 A | 8/1996 | Katsevich et al. |
| 5,717,211 A | 2/1998 | Katsevich |
| 5,881,123 A | 3/1999 | Tam |
| 7,590,216 B2 | 9/2009 | Katsevich |

OTHER PUBLICATIONS

Faridani et al., Introduction to local tomography.Contemp. Math., 278, Amer. Math. Soc, 2001, pp. 29-47.
Katsevich et al., Local Tomography: a New Concept in Computed Tompgraphy Reconstructions, 2011. pp. 1-4.
Katsevich, Cone beam local tomography, SIAM Journal on Applied Mathematics. 1999. vol. 59 (No. 6): 2224-2246.
Katsevich. Improved cone beam local tomography, Inverse Problems. 2006. vol. 22: 627-643.
Louis and Maass, Contour reconstruction in 3-D X-ray CT, IEEE Transactions on Medical Imaging. 1993. vol. 12 (No. 4): 764-769.
Moscariello et al., Coronary CT Angiography: Image Quality, Diagnostic Accuracy, and Potential for Radiation Does Reduction Using a Novel Iterative Image Reconstruction Technique—Comparison with Traditional Filtered Back Projection, Euro. Radiol. 2011. vol. 21: 2130-2138.
Park et al. Automatic Tube Potential Selection with Tube Current Modulation (APSCM) in coronary CT angiography: Comparison of image quality and radiation dose with conventional body mass index-based protocol. Journal of Cardiovascular Computed Tomography .2012. vol. 6: 184-190.

(Continued)

*Primary Examiner* — Atiba O Fitzpatrick
(74) *Attorney, Agent, or Firm* — Molly L. Sauter; Smith & Hopen, P.A.

(57) ABSTRACT

Methods, processes and systems of image reconstruction using variable filter length local tomography, for reconstructing internal body images in medical applications, and the like. The system and method of the present invention utilizes less radiation and less computer power than the prior art, without using iteration algorithms so that all target sizes from large to small can be reconstructed.

17 Claims, 3 Drawing Sheets

(56) References Cited

OTHER PUBLICATIONS

Raff. Radiation dose from coronary CT angiography: Five years of progress. Journal of Cardiovascular Computed Tomography .2010. vol. 4: 365-374.

Sato et al., Effect of radiation dose and adaptive statistical iterative reconstruction on image quality of pulmonary computed tomography. Jpn J Radiol. 2012. vol. 30:146-153.

Chen, Local volume reconstruction from width-truncated cone-beam projections by convolution backprojection, Optical Engineering. 2008. vol. 47 (Issue 1): 1-10.

SYSTEM AND METHOD OF VARIABLE FILTER LENGTH LOCAL TOMOGRAPHY

STATEMENT OF GOVERNMENT INTEREST

This invention was made with government support under NSF (National Science Foundation) award DMS-0806304, and DMS-1211164. The government has certain rights in this invention.

CROSS-REFERENCE TO RELATED APPLICATIONS

This application claims priority to co-pending U.S. patent application Ser. No. 13/722,383, entitled "Variable Filter Length Local Tomography", filed Dec. 20, 2012, the contents of which are herein incorporated in their entirety.

FIELD OF INVENTION

This invention relates to image reconstruction, and in particular to methods, processes and systems of image reconstruction using variable filter length local tomography, for reconstructing internal body images in medical applications, and the like.

BACKGROUND OF THE INVENTION

Recognition of the dangers of ionizing radiation has become more focused over time. The recent focus on reducing dose became more urgent with the advent of cardiac Computed Tomography (CT). See for example, Raff, G. L., Radiation dose from coronary CT angiography: Five years of progress. Journal of Cardiovascular Computed Tomography (2010) 4, 365-374. These are inherently high dose procedures. Attempts to reduce dose include adaptive iterative reconstructions and modulating the tube potential during the scan.

See for example, Sato, J., M. Akahane. S. Inano et al. Effect of radiation dose and adaptive statistical iterative reconstruction on image quality of pulmonary computed tomography. Jpn J Radiol (2012) 30:146-153; and Park, Y J Kim, J W Lee, et al. Automatic Tube Potential Selection with Tube Current Modulation (APSCM) in coronary CT angiography: Comparison of image quality and radiation dose with conventional body mass index-based protocol. Journal of Cardiovascular Computed Tomography (2012) 6, 184-190.

Suppose one is interested in reconstructing a region of interest (ROI) inside a patient. In our case the ROI is the cardiac region. Conventional (also known as global) reconstruction requires that the entire cross-section of the patient be irradiated. This means that during the scan one has to transmit x-rays through parts of the patient located far from the ROI. In the past 10-15 years, a group of algorithms called Local Tomography (LT) was developed. See, for example, Ramm A., and A. Katsevich, The Radon transform and local tomography, CRC Press, Boca Raton, Fla., 1996, and Katsevich, A. Improved cone beam local tomography, Inverse Problems 22 (2006). 627-643.

The main idea of LT is based on transmitting only those X-rays through the patient that intersect the Region of Interest (ROI) inside the patient. The X-rays that do not pass through the ROI are blocked from reaching the patient, which results in a reduction of the dose of a CT scan.

Conventional Computed Tomography (CT) reconstructs the distribution $\mu$ of the x-ray attenuation coefficient inside the object being scanned. Normally, $\mu$ is measured in Hounsfield units. Local Tomography (LT) computes not $\mu$, but $B\mu$, where B is some operator that enhances singularities of $\mu$ (e.g., edges). Thus, the information about the actual values of $\mu$ inside the ROI is not recovered.

In two dimensions the main mathematical basis for LT is provided by the following two formulas (A) and (B):

$$f_\Lambda = \frac{1}{4\pi} \int_0^{2\pi} g''(\alpha, \alpha \cdot x) d\alpha, \quad (A)$$

$$f_\Lambda = F^{-1}(|\xi| \tilde{f}(\xi)), \quad (B)$$

where $\tilde{f}$ is the Fourier transform of f; $F^{-1}$ is the inverse Fourier transform; and g represents the CT data.

The fact that the first formula, A, contains only one integral demonstrates that LT reconstruction is local. The presence of the growing factor $|\xi|$ in the second formula proves that LT enhances edges. The useful property of LT, which also follows from the second equation, is that it preserves all geometric features inside the ROI. In other words, the sharp features of $\mu$ (e.g., location of edges) coincide with sharp features of $B\mu$. See for example: Ramm A., and A. Katsevich, The Radon transform and local tomography, CRC Press. Boca Raton, Fla., 1996; and Faridani, A., K. Buglione, P. Huabsomboon, et al., Introduction to local tomography, Radon transforms and tomography. Contemp. Math. 278, Amer. Math. Soc. 2001, pp. 29-47. Thus, in some sense, LT is close to the gradient of the true image f.

In the cone beam setting (e.g., in helical scanning), the situation is more complicated. The reason is that B may add sharp features that are not present in $\mu$. See for example, Katsevich. A., Cone beam local tomography, SIAM Journal on Applied Mathematics (1999). 2224-2246. This manifests itself as artifacts. However, it was shown by one of the subject inventors that by choosing an appropriate direction of filtering, one can significantly reduce the strength of the artifacts and potentially reduce dose. See for example, Katsevich, A., Improved cone beam local tomography, Inverse Problems 22 (2006), 627-643.

In classical cone beam LT the convolution kernel is very short, because it is equivalent to computing some kind of derivative on the detector. See for example, Louis A. K., and P. Maass, Contour reconstruction in 3-D X-ray CT, IEEE Transactions on Medical Imaging 12 (1993), 764-769 and Katsevich, A., Improved cone beam local tomography, Inverse Problems 22 (2006), 627-643.

A main disadvantage of LT is that LT images look different from conventional CT images, which may result in a loss of diagnostic information. Since LT emphasizes edges and does not reconstruct $\mu$ in Hounsfield units it is sometimes hard to differentiate between tissue types and even see the presence of contrast.

Thus, the need exists for solutions to the above problems with the prior art.

SUMMARY OF INVENTION

A primary objective of the present invention is to provide methods, processes and systems for image reconstruction of internal body images in medical applications, and the like, which allows for both differentiation between tissue types and detect the presence of contrast in the blood.

A secondary objective of the present invention is to provide methods, processes and systems for image reconstruction of internal body images in medical applications, and the like, that uses less radiation (less x-rays) to target body areas for image reconstruction than prior art techniques.

A third objective of the present invention is to provide methods, processes and systems for image reconstruction of internal body images in medical applications, and the like, to reconstruct in close to real time (in seconds).

A fourth objective of the present invention is to provide methods, processes and systems for image reconstruction of internal body images in medical applications, and the like, that do not use iterative algorithms, and use less computational power than that needed to perform iterative image reconstruction.

A fifth objective of the present invention is to provide methods, processes and systems for image reconstruction of internal body images in medical applications, and the like, with improved spatial resolution and contrast resolution that doesn't miss small targets.

A sixth objective of the present invention is to provide methods, processes and systems for image reconstruction using variable filter length local tomography, for reconstructing internal body images in medical applications, and the like.

A seventh objective of the present invention is to provide methods, processes and systems for image reconstruction of internal body images in medical applications, and the like, which would be a compromise between the local and global tomographics.

An eighth objective of the present invention is to provide methods, processes and systems for image reconstruction of internal body images in medical applications, and the like, to find a convolution kernel, which is sufficiently short so that only a small neighborhood of the ROI (Region of Interest) would need to be irradiated resulting in a reduced dose while assuring that, the kernel was sufficiently long so that reconstructed images could differentiate tissue types.

A method for reconstructing an image from cone beam (CB) projection data provided by at least one detector, comprising the steps of: a. scanning an object to collect cone-beam projection data; b. loading the CB (cone beam) projection data into a computer; c. using the CB projection data for reconstructing an image of the object; and d. repeat loading and using additional CB projection data until image reconstruction is finished at all reconstruction points x, wherein during step c only truncated CB data are used at one or more reconstruction points x inside the object, wherein the said truncated CB data are defined as data which are insufficient for theoretically exact reconstruction at a point x; wherein the step c. of reconstructing includes the substeps of: c.i. filtering the truncated CB data; c.ii. back-projection updating of the image being reconstructed; wherein the substep c.i. uses a filter of length longer than the length of a filter associated with computing a derivative (typically 2-4 points), but shorter than the length of a filter associated with theoretically exact reconstruction (of infinite length or of length equal to a support of the object along the line of filtration); wherein the image reconstructed in step d is not intended to approximate a theoretically exact reconstruction, but allows differentiation of tissue types that comprise the object being scanned.

The reconstruction points can be confined to a region of interest (ROI) strictly in the interior of the object being scanned.

The substep c.i. of filtering can use a filter, which is different from a truncated version of a ramp filter;

The filter can be modified so that differentiation of materials that constitute the object being scanned using the reconstructed image is improved:

The filter can be K(j) and the filter satisfies the equation $$\sum_{j=-n}^{n} K(j) = 0,$$

where n is the filter half-width;

The loading step can include the step of: denoting the projection data as $D_f(s,u,v)$, CB projection corresponds to source position $y(s_k)$, and detector surface corresponding to the x-ray source located at $y(s_k)$ is denoted $DP(s_k)$.

The filtering step can include the step of: calculating filtered values according to:

$$g_1(s_k, i_c, i_r) = \sum_{j=-n}^{n} D_f(s_k, i_c - j, i_r) K(j),$$

where K(j) is the filter, n is the half-width of the filter, and $g_1(s_k,i_c,i_r)$ is the filtered data, $i_r$ is the index of a detector row, $i_c$ is the index of a detector column, and $D_f(s_k,i_c,i_r)$ is the CB projection data in the $(i_c,i_r)$ location on the detector.

The backprojection step c. ii can include the steps of:
c. ii (a) fixing a reconstruction point x, which represents a point inside the patient where it is required to reconstruct the image;
c. ii (b) finding the projection $\hat{x}$ of x onto a detector $DP(s_k)$, with $(i_c^x, i_r^x)$ be the row- and column-coordinates of $\hat{x}$ on the detector;
c. ii (c) if $\hat{x}$ projects onto the detector, the said filtered CB data affects the image at x, go to steps c. ii (e), c. ii (f), c. ii (g), c. ii (h);
c. ii (d) If $\hat{x}$ projects outside the detector, then said filtered CB data are not used for image reconstruction at x, then go to step (a) for another reconstruction point;
c. ii (e) identifying rows and columns on the detector that are close to the said projection $\hat{x}$ to determine values of $g_1(s_k,i_c,i_r)$ for $(i_c,i_r)$ close to $(i_c^x,i_r^x)$;
c. ii (f) estimating value of $g_1(s_0,i_c^x,i_r^x)$ with interpolation from the said values of $g_1(s_0,i_c,i_r)$ for $(i_c,i_r)$ close to $(i_c^x,i_r^x)$;
c. ii (g) computing contribution from the said filtered CB data to the image being reconstructed at the point x by multiplying $g_1(s_k,i_c^x,i_r^x)$ by a weight function $w(s_k,x)$;
c. ii (h) adding the contribution to the image being reconstructed at the point x according to a pre-selected scheme; and
c. ii (i) repeating above steps for fixing another different reconstruction point x until all reconstruction points have back-projection.

The following detailed description of the presently preferred embodiments which are illustrated schematically in the accompanying drawings.

DETAILED DESCRIPTION OF THE PREFERRED EMBODIMENT

Figure 1:
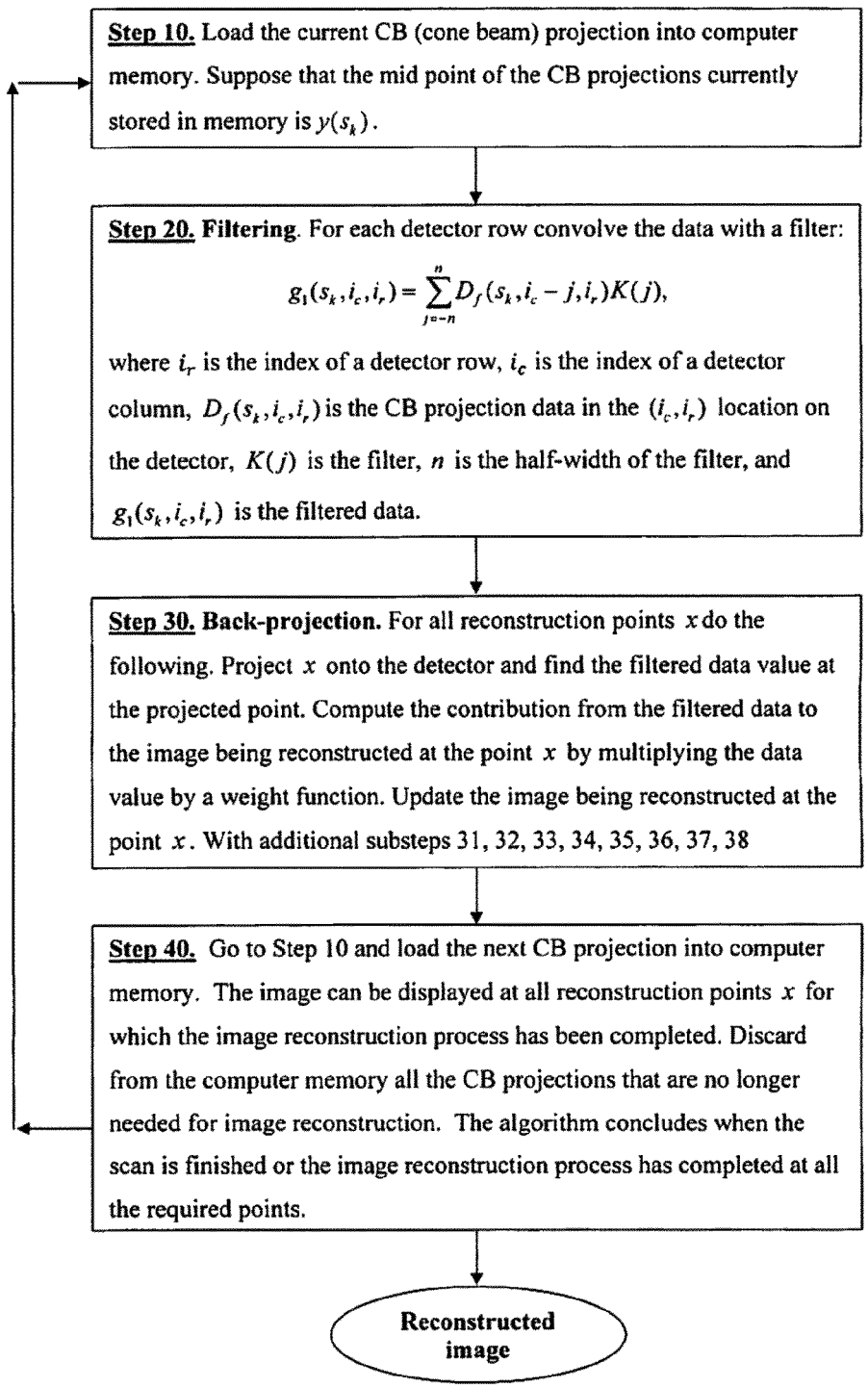
FIG. 1 is a flowchart of the steps for reconstruction using variable length local tomography in accordance with an embodiment of the present invention

Before explaining the disclosed embodiments of the present invention in detail it is to be understood that the invention is not limited in its applications to the details of the particular arrangements shown since the invention is capable of other embodiments. Also, the terminology used herein is for the purpose of description and not of limitation.

One of the subject inventors, Dr. Alexander Katsevich, has patented image reconstruction that includes local tomography. See for example, U.S. Pat. Nos. 5,539,800; 5,550,892; 5,717,211 all to Katsevich, which in their entirety are all incorporated by reference. Additionally, Dr. Katsevich has patented an invention in cone beam local tomography. See for example. U.S. Pat. No. 7,590,216 to Katsevich, which in its' entirety is also incorporated by reference. The prior patents include but are not limited to collecting cone beam (CB) projection data from at least one detector, in order to reconstruct images of an object.

The subject invention can use the same equipment described in these patents with a novel computer run algorithm which is described below.

For the subject invention, the mathematical description of the algorithm is given by the following formula:

$$f_1(x) = \int w(s,x) \int D_f(s, u(s,x)-u, v) K(u) du \, ds, \quad (0.1)$$

where s is a parameter along the source trajectory, $f_1$ is the image to be reconstructed, x is a reconstruction point, K(u) is a reconstruction kernel, w(s,x) is a weight function, u and v are row- and column-coordinates on the detector, respectively, u(s,x) and v(s,x) are the row- and column-coordinates of the projection of a reconstruction point x on the detector corresponding to the source position y(s), and $D_f$ is the cone-beam data. In discrete form, equation (1.1) can be written as follows:

$$f_1(x) = \sum_k w(s_k, x) \sum_{j=-n}^{n} D_f(s_k, u(s_k, x) - u_j, v) K(u_j) \Delta u \Delta s, \quad (1.2)$$

where n is the half-length of the filter, and $\Delta u$ and $\Delta s$ are the step-sizes along the u and s variables, respectively.

The Local tomography is quite flexible and a wide variety of weight functions and reconstruction kernels is possible. For example, we can choose $$K(j) = \begin{cases} 0, & \text{if } |j| \text{ is even and } j \neq 0 \text{ or } |j| > n; \\ 1/j^2, & \text{if } |j| \text{ is odd and } |j| \leq n; \\ -2 \sum_{i=1}^{L} (1/i^2), & j = 0. \end{cases} \quad (1.3)$$

An example of a weight function is as follows:

$$w(s,x) = (R - (x_1 y_1(s) + x_2 y_2(s))/R)^{-1},$$

where R is the radius of the helix, $x_1$, $x_2$ are the in-plane coordinates of a reconstruction point, and $y_1(s)$, $y_2(s)$ are the in-plane coordinates of the current source position y(s).

The interval of integration in (1.1) and, correspondingly, the range of summation in (1.2), may depend on the specifics of the image reconstruction problem. In the case of cardiac CT when image reconstruction at a certain cardiac phase is required, the weight function w(s,x) will include additional factors that go to zero farther away from the desired phase. More generally, the weight function may include factors that go to zero near the detector boundary to reduce data truncation artifacts. The cone-beam data $D_f(s,u,v)$ are measured by the detector at a discrete set of points $u = \Delta u i_c$, $v = \Delta v i_r$, where $i_r$ denotes the index of a detector row, and $i_c$ denotes the index of a detector column. Thus, in what follows, for simplicity the detector data are denoted $D_f(s, i_c, i_r)$.

As stated, equation (1.1) does not involve weighting of the CB data $D_f(s,u,v)$ prior to convolution. Other embodiments of the algorithm are possible, in which the CB data are multiplied by a weight factor prior to the convolution. Regardless of whether the CB data are weighted prior to convolution or not, in both cases we say that the CB data are filtered.

The filter K(j) of the present invention is similar to the filter described by equation (6) in Z. Chen, Local volume reconstruction from width-truncated cone-beam projections by convolution backprojection, Optical Engineering, volume 47 (2008), issue 1. The main difference between the two filters is the value of K(0). As is known, the filter needs to satisfy the equation $$\sum_{j=-\infty}^{\infty} K(j) = 0. \quad (1.4)$$

The filter in equation (1.3) satisfies equation (1.4). In an effort to make reconstruction from truncated data as close to conventional reconstruction as possible, in paper Z. Chen, Local volume reconstruction from width-truncated cone-beam projections by convolution backprojection, Optical Engineering, volume 47 (2008), issue 1, the author truncates the conventional filter at some length and keeps all other filter values the same. Consequently, as the filter length n becomes increasingly small, the filter in Z. Chen, Local volume reconstruction from width-truncated cone-beam projections by convolution backprojection, Optical Engineering, volume 47 (2008), issue 1, violates equation (1.4) more strongly and the corresponding reconstructions become increasingly worse as confirmed by the following quote from the paper: " . . . a short kernel incurs a large error, as revealed in FIG. 2b".

Conceptually, the main difference between the approach in Z. Chen, Local volume reconstruction from width-truncated cone-beam projections by convolution backprojection, Optical Engineering, volume 47 (2008), issue 1, and the approach in the present invention is that the former attempts to make reconstruction from truncated data as close to conventional reconstruction as possible, which, in particular, necessitates the use of data extrapolation. In the present invention the goal is to come up with an image that only looks qualitatively similar to conventional reconstruction. In particular, the algorithm of the present invention can be used with non-truncated data as well.

The main steps for running the algorithm in detail are in steps 10-40. FIG. 1 is a flowchart of the steps for reconstruction using variable length tomography.

Step 10. Load the current CB (cone beam) projection $D_f(s, u, v)$ into computer memory. Suppose that this CB projection corresponds to the source position $y(s_k)$. The detector surface corresponding to the x-ray source located at $y(s_k)$ is denoted $DP(s_k)$.

Step 20: Filtering. For each detector row convolve the data with a filter. Let $i_r$ be the index of a detector row, $i_c$ be the index of a detector column, and let $D_f(s_k, i_c, i_r)$ be the CB projection data in the $(i_c, i_r)$ location on the detector. We use the following equation (cf. equation (1.2)):

$$g_1(s_k, i_c, i_r) = \sum_{j=-n}^{n} D_f(s_k, i_c - j, i_r) K(j),$$

where K(j) is the filter, n is the half-width of the filter, and $g_1(s_k, i_c, i_r)$ is the filtered data.

By itself the filtering step is well known in the field and can be implemented, for example, as shown and described in U.S. Pat. No. 5,881,123 to Tam, which is incorporated by reference. Alternative implementation of the convolution can be based on the Fast Fourier Transform (FFT).

Step 30: Backprojection.

Step 31. Fix a reconstruction point x, which represents a point inside the patient where it is required to reconstruct the image.

Step 32. Find the projection $\hat{x}$ of x onto the detector surface $DP(s_k)$ Let $(i_c^x, i_r^x)$ be the row- and column-coordinates of $\hat{x}$ on the detector.

Step 33. If $\hat{x}$ projects onto the detector, the said filtered CB data affects the image at x and one performs Steps 34-38. If $\hat{x}$ projects outside the detector, then the said filtered CB data are not used for image reconstruction at x. In this case go back to Step 31 and choose another reconstruction point.

Step 34. Identify the rows and columns on the detector that are close to the said projection $\hat{x}$. This will give a few values of $g_1(s_k, i_c, i_r)$ for $(i_c, i_r)$ close to $(i_c^x, i_r^x)$.

Step 35. With interpolation estimate the value of $g_1(s_0, i_c^x, i_r^x)$ from the said values of $g_1(s_0, i_c, i_r)$ for $(i_c, i_r)$ close to $(i_c^x, i_r^x)$.

Step 36. Compute the contribution from the said filtered CB data to the image being reconstructed at the point x by multiplying $g_1(s_k, i_c, i_r)$ by a weight function $(s_k, x)$.

Step 37. Add the said contribution to the image being reconstructed at the point x according to a pre-selected scheme (for example, the Trapezoidal scheme) for approximate evaluation of the integral in equation (1.1) according to (1.2).

Step 38. Go to Step 31 and choose a different reconstruction point x.

Step 40. Go to Step 10 and load the next CB projection into computer memory. The image can be displayed at all reconstruction points x for which the image reconstruction process has been completed (that is, all the subsequent CB projections are not needed for reconstructing the image at those points). Discard from the computer memory all the CB projections that are not needed for image reconstruction at points where the image reconstruction process has not completed. The algorithm concludes when the scan is finished or the image reconstruction process has completed at all the required points.

Figure 2:
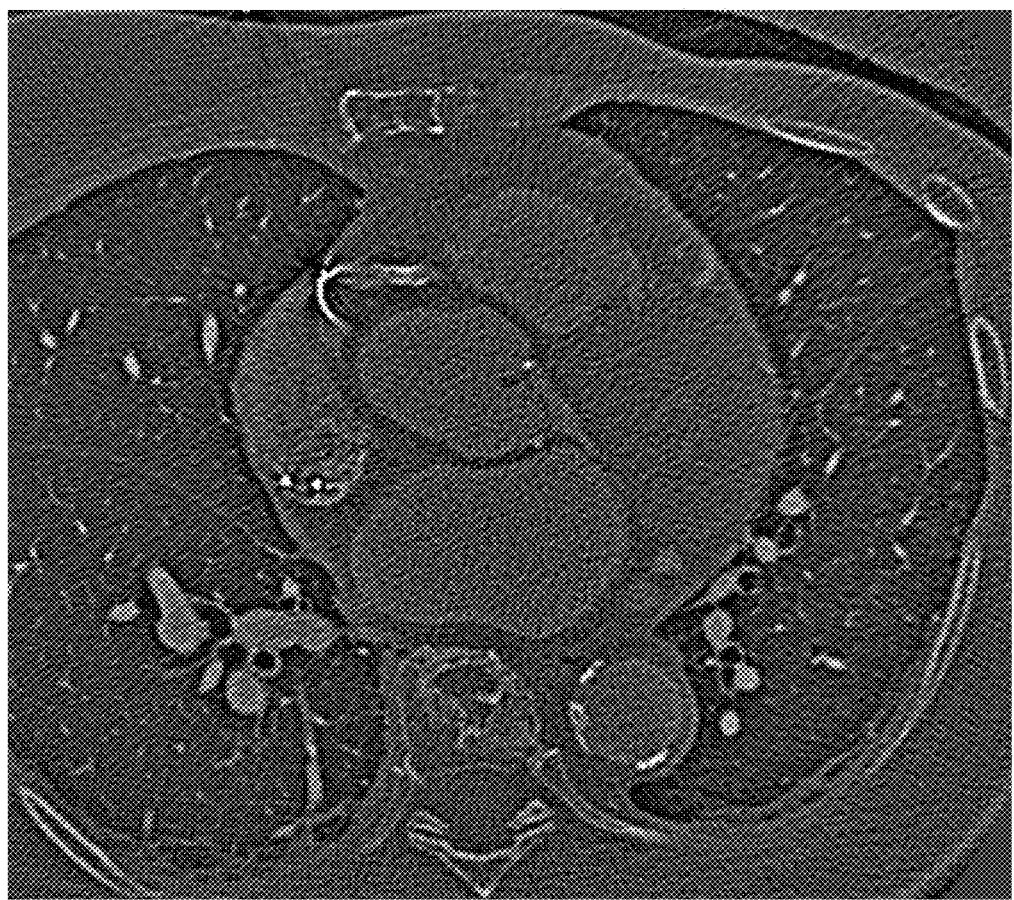
FIG. 2 shows an image reconstruction with the prior art local tomography.

FIG. 2 shows an image reconstruction with the prior art local tomography.

Figure 3:
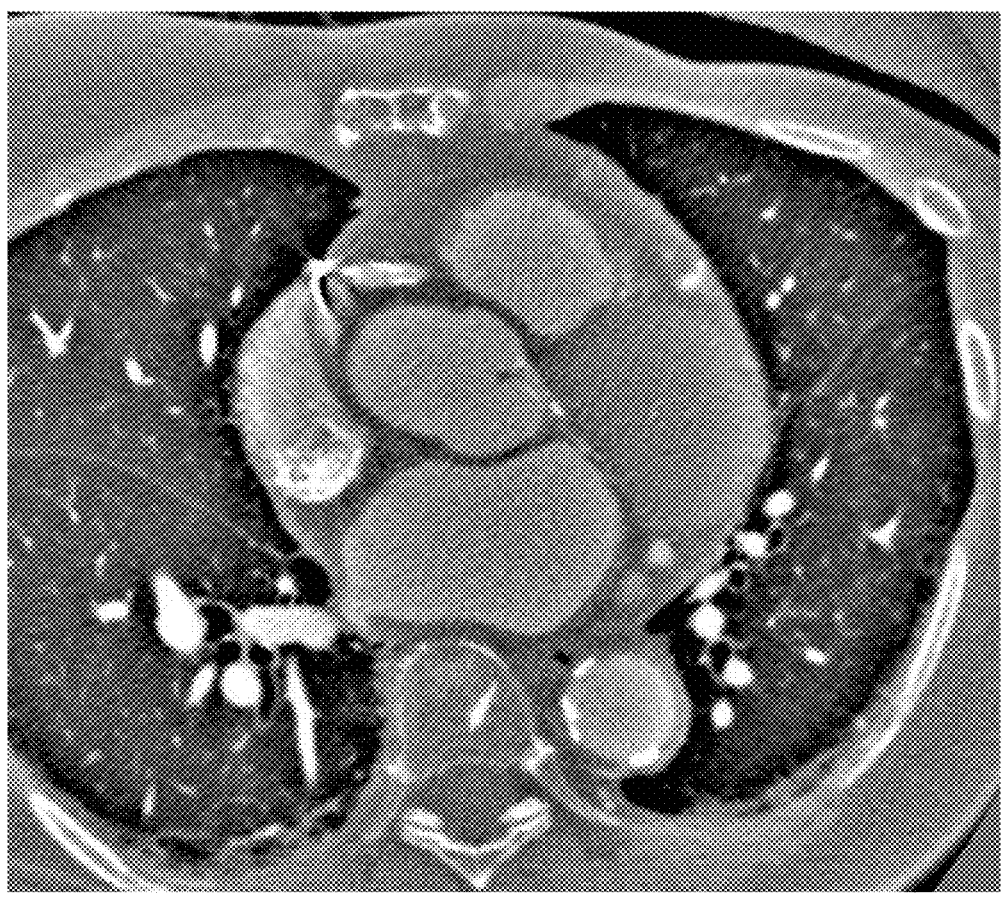
FIG. 3 shows an image reconstruction using the invention variable filter length local tomography in accordance with an embodiment of the present invention.

FIG. 3 shows an image reconstruction using the invention variable filter length local tomography. It is clearly seen that the image in FIG. 3 is much more informative than that in FIG. 2. Different tissue types can be easily differentiated, and contrast media inside blood vessels is visible.

As is seen from the description of Steps 10-40, the algorithm of the present invention is computationally efficient. It contains steps like filtering, backprojection, multiplication by a weight function, and the like. Most importantly, for each source position the filtering on the detector is performed along a one-parametric family of curves. The algorithms of prior art that reconstruct images from truncated data are generally computationally expensive in view of the extra computer power, time and memory needed. The invention can consist of minimal steps that do not require the extra computer power, time and memory needed. For example, filtered back projection is an example of an algorithm that only requires minimal extra steps in addition to filtering and backprojection to operate. The minimal steps can include but are not limited to multiplication of data (non-filtered and filtered) by a weight function, linear interpolation, smoothing, and the like. The invention does not include any iterative steps, filling in of the missing data, using wavelets, curvelets, and the like.

A study of image reconstruction using the novel algorithm occurred at the Texas Medical Center in Houston. The first part of this study was retrospective analysis of patients comparing anatomy on selected slices of the coronary computed tomography angiogram (CCTA) with reconstructions using LT tomography at the same level(s). Subsequently, to test the feasibility of viewing anatomy that was comparable on the two types of reconstructions, other subjects who would consent were prospectively recruited from all patients that presented to the hospital CT scanner in whom a cardiac computed tomography angiogram was ordered by the referring physician.

Following patient consent, scans were obtained on a CB CT scanner utilizing helical scanning and dose modulated retrospective ECG gating. The contrast agent was utilized.

For all cases raw CT data was stripped of identifying information, assigned a study number, and transferred to an external hard drive for subsequent analysis by the local tomography (LT) algorithm that comprise this invention. In a parallel fashion the scanner raw CT data was processed and reconstructed in a routine manner and transferred to a CT visualization workstation for review and clinical reading and report by a radiologist or cardiologist responsible for the normal workflow. For the study, this reconstructed data was also stripped of patient identifiers and used for the study. Two experienced readers compared the LT images and the conventional CT images for diagnostic accuracy, spatial resolution, and contrast resolution and an assessment of whether all lesions seen on the conventional CTA were identified by the LT reconstructed images.

An estimate was made about the range of potential radiation dose savings based upon the individual geometry of the scan regions of interest.

Feedback from the two experienced readers from the Texas Medical Center showed that the LT of the present invention provides excellent anatomical rendering, including differentiation of tissue types, and the contrast is clearly visible as well. Our estimations showed that LT has potential to decrease radiation by 50%.

Although the invention is primarily directed to image reconstruction of internal body images (of cardiac and other organs/body parts), the invention can be used in other applications. For example, the novel algorithm can be used for security screening and non-destructive evaluation of cargo at airports and shipping ports. The invention can be used for scanning small and large machine parts for defects. The invention can further be used in wood working applications to determine the location of knots and cracks.

The algorithm of the invention reconstructs an image at a reconstruction point x using tomographic data corresponding to integrals along lines passing through a neighborhood of x. Therefore the algorithm is suitable for reconstructing a region of interest inside an object from truncated data. On the other hand, the algorithm can be used for reconstructing the entire object from non-truncated data since it can visualize certain features inside the object better than the traditional theoretically exact methods (iterative and non-iterative).

Hardware and Software Infrastructure Examples

The present invention may be embodied on various computing platforms that perform actions responsive to software-based instructions. The following provides an antecedent basis for the information technology that may be utilized to enable the invention.

The computer readable medium described in the claims below may be a computer readable signal data medium or a computer readable data storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires or wireless connection, a portable computer diskette or other data storage device, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, other data storage device, or any suitable combination of the foregoing. In the context of this document, a computer readable storage medium may be any tangible medium that can contain, or store a program for use by or in connection with an instruction execution system, apparatus, or device.

A computer readable signal data medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal data medium may be any computer readable medium that is not a computer readable storage medium and that can communicate, propagate, or transport a program for use by or in connection with an instruction execution system, apparatus, or device.

Program code embodied on a computer readable data medium may be transmitted using any appropriate medium, including but not limited to wireless, wire-line, optical fiber cable, radio frequency, etc., or any suitable combination of the foregoing. Computer program code for carrying out operations for aspects of the present invention may be written in any combination of one or more programming languages, including an object oriented programming language such as Java, C#, C++, Fortran, scripting languages, or the like and conventional procedural programming languages, such as the "C" programming language or similar programming languages.

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

GLOSSARY OF CLAIM TERMS

Back-projection updating: use of a backprojection algorithm for reconstruction of an image. Generally, backprojection refers to the step of using projection data for updating the image volume being reconstructed.

Computer: a general purpose device that can be programmed to carry out a set of arithmetic or logical operations.

Cone beam (CB) projection data: two-dimensional data provided by a detector array integral to a computed tomography (CT) imaging system.

Curvelets: a higher dimensional generalization of the wavelet transform designed to represent images at different scales and different angles.

Detector: a two-dimensional array detector having a plurality of rows and a plurality of columns.

Filtering: a mathematical process by which one-, two-, or higher-dimensional data arrays are transformed with the purpose of changing the frequency content of the said arrays. Those purposes may include, but are not limited to suppression of noise and smoothing, edge enhancement and resolution recovery.

Image reconstruction: creation of a two- or three-dimensional image from projection data.

Ramp filter: a high pass filter, whose graph in the frequency domain looks like a linearly increasing ramp function. To avoid artifacts, at the highest frequencies the ramp filter may go to zero in a smooth fashion.

Truncated CB data: CB data which is insufficient for theoretically exact reconstruction at a given point.

Wavelets: a class of functions, which is used to localize a given function both in space and scale.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

What is claimed is:

1. A method for reconstructing an image from cone beam (CB) projection data provided by at least one detector, the method comprising:

scanning an object to collect cone-beam (CB) projection data;

loading the CB projection data into a computer;

reconstructing an image of the object using the CB projection data; and repeatedly loading and using additional CB projection data until image reconstruction is finished at all reconstruction points x;
  wherein reconstructing an image of the object using the CB projection data comprises only using truncated CB data at one or more reconstruction points x inside the object,
  wherein the truncated CB data is defined as data which is insufficient for theoretically exact reconstruction at a point x;
  wherein reconstructing an image of the object using the CB data further comprises:
    filtering the truncated CB data; and
    back-projection updating of the image being reconstructed;
  wherein filtering the truncated CB data uses a filter of a length longer than the length of a filter associated with computing a derivative, but shorter than the length of a filter associated with theoretically exact reconstruction (of infinite length or of length equal to a support of the object along the line of filtration);
  wherein the image reconstructed by repeatedly loading and using additional CB projection data is not intended to approximate a theoretically exact reconstruction, but allows differentiation of tissue types that comprise the object being scanned, and
  wherein the computer does not process the projection data for the image reconstruction using iterative steps, does not perform filling in of the missing data, and does not use wavelets and curvelets.

2. The method of claim 1, wherein the reconstruction points are confined to a region of interest (ROI) strictly in the interior of the object being scanned.

3. The method of claim 1, wherein filtering the truncated data uses a filter, which is different from a truncated version of a ramp filter.

4. The method of claim 3, wherein the filter is modified so that differentiation of materials that constitute the object being scanned using the reconstructed image is improved.

5. The method of claim 3, wherein the filter is K(j) and the filter satisfies the equation $$\sum_{j=-n}^{n} K(j) = 0,$$

where n is the filter half-width.

6. The method of claim 1, wherein loading the CB projection data into the computer further comprises, denoting the projection data as $D_f(s,u,v)$, CB projection corresponds to source position $y(s_k)$, and detector surface corresponding to the x-ray source located at $y(s_k)$ is denoted $DP(s_k)$.

7. The method of claim 6, wherein the filtering the truncated CB data further comprises, calculating filtered values according to:

$$g_1(s_k, i_c, i_r) = \sum_{j=-n}^{n} D_f(s_k, i_c - j, i_r) K(j),$$

where K(j) is the filter, n is the half-width of the filter, and $g_1(s_k,i_c,i_r)$ is the filtered data, $i_r$ is the index of a detector row, $i_c$ is the index of a detector column, and $D_f(s_k,i_c,i_r)$ is the CB projection data in the $(i_c,i_r)$ location on the detector.

8. The method of claim 7, wherein back-projection updating of the image being constructed further comprises:
  fixing a reconstruction point x, which represents a point inside the patient where it is required to reconstruct the image;
  finding the projection $\hat{x}$ of x onto a detector $DP(s_k)$, with $(i_c^x, i_r^x)$ be the row- and column-coordinates of $\hat{x}$ the detector;
  if $\hat{x}$ projects onto the detector, the filtered CB data affects the image at x, the method further comprises;
    identifying rows and columns on the detector that are close to the said projection $\hat{x}$ to determine values of $g_1(s_k,i_c,i_r)$ for $(i_c,i_r)$ close to $(i_c^x,i_r^x)$;
    estimating value of $g_1(s_0,i_c^x,i_r^x)$ with interpolation from the said values of $g_1(s_0,i_c,i_r)$ for $(i_c,i_r)$ close to $(i_c^x,i_r^x)$;
    computing contribution from the said filtered CB data to the image being reconstructed at the point x by multiplying $g_1(s_k,i_c^x,i_r^x)$ by a weight function $w(s_k,x)$;
    adding the contribution to the image being reconstructed at the point x according to a pre-selected scheme;
  or, if $\hat{x}$ projects outside the detector, then the filtered CB data is not used for image reconstruction at x, then fixing another reconstruction point x; and
  repeatedly fixing another different reconstruction point x until all reconstruction points have back-projection.

9. A method for reconstructing an image from cone beam (CB) projection data provided by at least one detector, comprising the steps of:
  collecting cone-beam (CB) projection data from an object being scanned;
  storing the CB projection data in a computer;
  reconstructing an image of the object using the CB projection data; and
  repeatedly loading and reconstructing the image until image reconstruction is finished at all reconstruction points x,
    wherein during reconstructing an image of the object using the CB projection data only truncated CB data at one or more reconstruction points x inside the object,
    wherein the truncated CB data is defined as data which is insufficient for theoretically exact reconstruction at a point x;
  wherein reconstructing an image of the object using the CB projection data further comprises:
    filtering the truncated CB data; and
    back-projection updating of the image being reconstructed,
    wherein filtering the truncated CB data uses a filter of length longer than the length of a filter associated with computing a derivative, but shorter than the length of a filter associated with theoretically exact reconstruction (of infinite length or of length equal to a support of the object along the line of filtration);
  wherein the image reconstructed by repeatedly loading and using additional CB projection data is not intended to approximate a theoretically exact reconstruction, but allows differentiation of tissue types that comprise the object being scanned,
  wherein the computer does not process the projection data for the image reconstruction using iterative steps, does not perform filling in of the missing data, and does not use wavelets and curvelets.

10. The method of claim 9, wherein the reconstruction points are confined to a region of interest (ROI) strictly in the interior of the object being scanned.

11. The method of claim 9, wherein filtering the CB data uses a filter, which is different from a truncated version of a ramp filter.

12. The method of claim 11, wherein the filter is modified so that differentiation of materials that constitute the object being scanned using the reconstructed image is improved.

13. The method of claim 11, wherein the filter is K(j) and the filter satisfies the equation $$\sum_{j=-n}^{n} K(j) = 0,$$

where n is the filter half-width.

14. The method of claim 9, wherein storing the CB projection data in a computer, further comprises, denoting the projection data as $D_f(s,u,v)$, CB projection corresponds to source position $y(s_k)$, and detector surface corresponding to the x-ray source located at $y(s_k)$ is denoted $DP(s_k)$.

15. The method of claim 14, wherein filtering the truncated CB data further comprises:
  calculating filtered values according to:

$$g_1(s_k, i_c, i_r) = \sum_{j=-n}^{n} D_f(s_k, i_c - j, i_r) K(j),$$

where K(j) is the filter, n is the half-width of the filter, and $g_1(s_k,i_c,i_r)$ is the filtered data, $i_r$ is the index of a detector row, $i_c$ is the index of a detector column, and $D_f(s_k,i_c,i_r)$ is the CB projection data in the $(i_c,i_r)$ location on the detector.

16. The method of claim 15, wherein back-projection updating of the image being reconstructed further comprises:
  fixing a reconstruction point x, which represents a point inside the patient where it is required to reconstruct the image;
  finding the projection $\hat{x}$ of x onto a detector $DP(s_k)$, with $(i_c^x, i_r^x)$ be the row- and column-coordinates of $\hat{x}$ on the detector;
  if $\hat{x}$ projects onto the detector, the filtered CB data affects the image at x, the method further comprises;
    identifying rows and columns on the detector that are close to the said projection $\hat{x}$ to determine values of $g_1(s_k,i_c,i_r)$ for $(i_c,i_r)$ close to $(i_c^x,i_r^x)$;
    estimating value of $g_1(s_0,i_c^x,i_r^x)$ with interpolation from the said values of $g_1(s_0,i_c,i_r)$ for $(i_c,i_r)$ close to $(i_c^x,i_r^x)$;
    computing contribution from the said filtered CB data to the image being reconstructed at the point x by multiplying $g_1(s_k,i_c,i_r)$ by a weight function $w(s_k,x)$;
    adding the contribution to the image being reconstructed at the point x according to a pre-selected scheme;
  or, if $\hat{x}$ projects outside the detector, then the filtered CB data is not used for image reconstruction at x, then fixing another reconstruction point x; and
  repeatedly fixing another different reconstruction point x until all reconstruction points have back-projection.

17. A computer-readable non-transitory storage medium storing a program causing a computer program to execute a method for reconstructing an image from cone beam (CB) projection data, the method comprising:
  storing cone beam (CB) projection data provided by at least one detector coupled to the computer;
  reconstructing an image of the object using the CB projection data and to repeatedly store and use additional CB projection data until image reconstruction is finished at all reconstruction points x;
    wherein reconstructing an image of the object using the CB projection data comprises only using truncated CB data at one or more reconstruction points x inside the object,
    wherein the truncated CB data is defined as data which is insufficient for theoretically exact reconstruction at a point x;
    wherein reconstructing an image of the object using the CB data further comprises:
      filtering the truncated CB data; and
      back-projection updating of the image being reconstructed;
    wherein filtering the truncated CB data uses a filter of a length longer than the length of a filter associated with computing a derivative, but shorter than the length of a filter associated with theoretically exact reconstruction (of infinite length or of length equal to a support of the object along the line of filtration);
    wherein the image reconstructed by repeatedly loading and using additional CB projection data is not intended to approximate a theoretically exact reconstruction, but allows differentiation of tissue types that comprise the object being scanned, and
    wherein the computer does not process the projection data for the image reconstruction using iterative steps, does not perform filling in of the missing data, and does not use wavelets and curvelets.

* * * * *

UNITED STATES PATENT AND TRADEMARK OFFICE
CERTIFICATE OF CORRECTION

PATENT NO. : 8,929,637 B1
APPLICATION NO. : 14/080099
DATED : January 6, 2015
INVENTOR(S) : Alexander Katsevich et al.

Page 1 of 1

It is certified that error appears in the above-identified patent and that said Letters Patent is hereby corrected as shown below:

In the claims,

Claim 2, Column 11, Line 33, should read:
points are confined to a region of interest (ROI) strictly in the Claim 16, Column 14, Line 3, should read:
tiplying  by a weight function $w(s_k,x)$;

Signed and Sealed this
Twenty-eighth Day of April, 2015

Michelle K. Lee
*Director of the United States Patent and Trademark Office*